Figure 1:
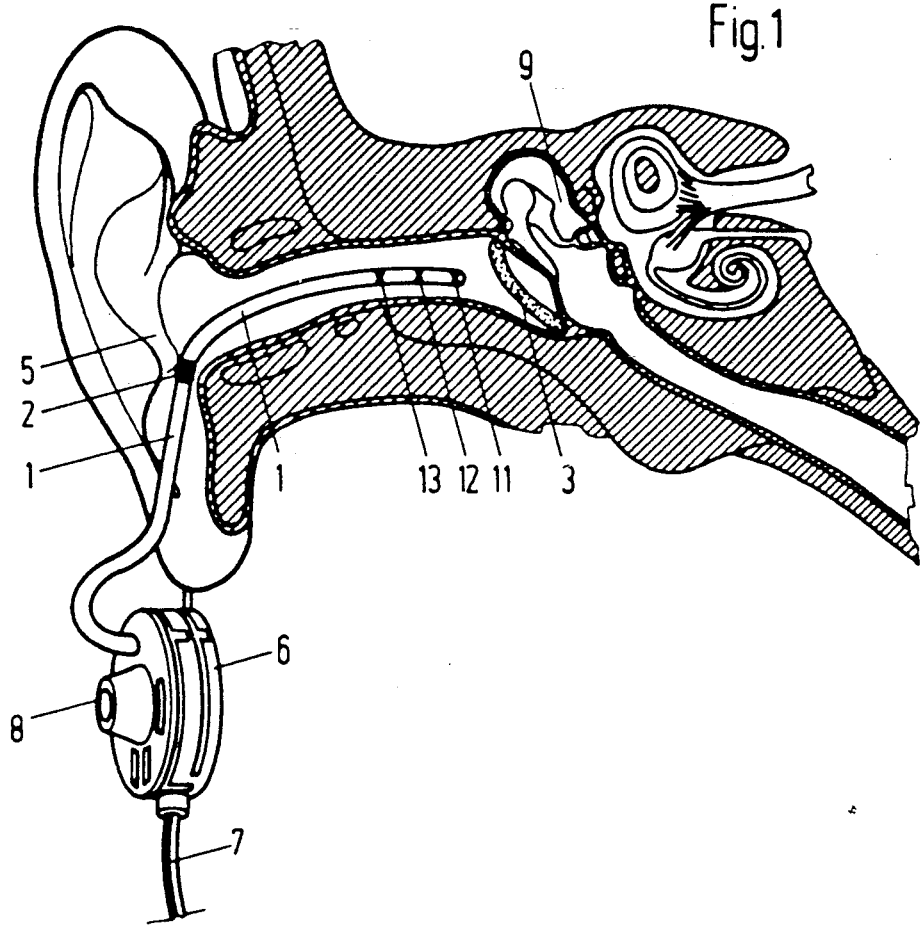

United States Patent [19]

Northeved et al.

[11] Patent Number: 5,044,373
[45] Date of Patent: Sep. 3, 1991

[54] METHOD AND APPARATUS FOR FITTING OF A HEARING AID AND ASSOCIATED PROBE WITH DISTANCE MEASURING MEANS

[75] Inventors: Allan Northeved, Farum; Torsten Johnsen, Copenhagen, both of Denmark

[73] Assignee: GN Danavox A/S, Copenhagen, Denmark

[21] Appl. No.: 469,221

[22] Filed: Jan. 24, 1990

[30] Foreign Application Priority Data

Feb. 1, 1989 [DK] Denmark ............................ 458/89

[51] Int. Cl.⁵ ............................................... A61B 5/12
[52] U.S. Cl. .................................................... 128/746
[58] Field of Search ................. 128/746; 181/130, 135

[56] References Cited

U.S. PATENT DOCUMENTS 4,809,708  3/1989  Geisler et al. ..................... 128/746

Primary Examiner—Kyle L. Howell
Assistant Examiner—Kevin Pontius
Attorney, Agent, or Firm—Merchant & Gould Smith, Edell, Welter & Schmidt

[57] ABSTRACT

The invention relates to the measuring of sound pressure levels in the auditory canal of a person in connection with the fitting of a hearing aid. An apparatus for this purpose comprises a measuring probe (1) which is introduced into the auditory canal, a microphone (6) coupled to the measuring probe (1), a data processing unit (14) with display (15) and printer (15'), a reference microphone (8) and a source of sound (10). In order to be able to position the measuring probe (1) precisely in the auditory canal, the probe is configured with means for measuring the distance from the free end of the probe to the ear drum which employs either sound, electromagnetic waves or light.

15 Claims, 5 Drawing Sheets

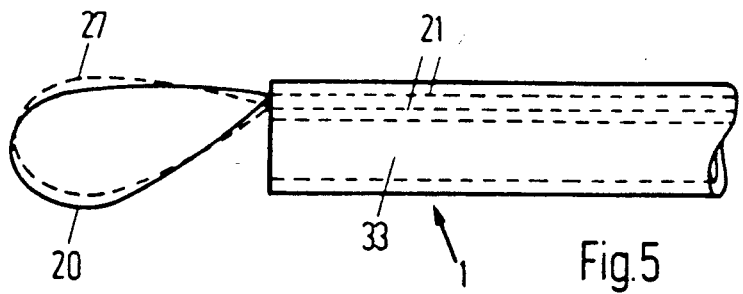
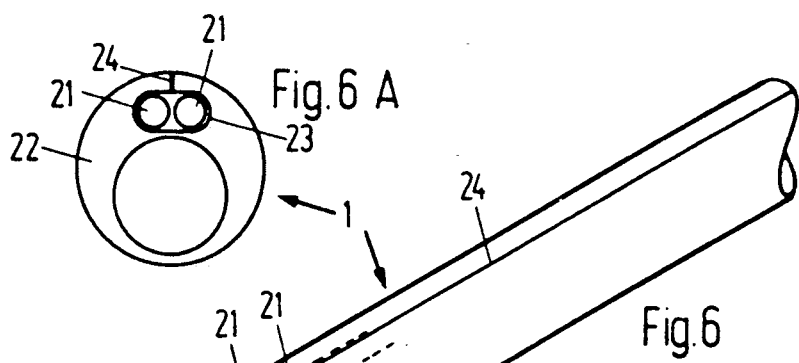
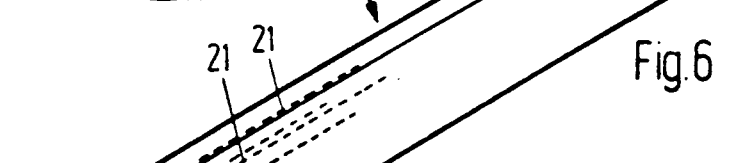
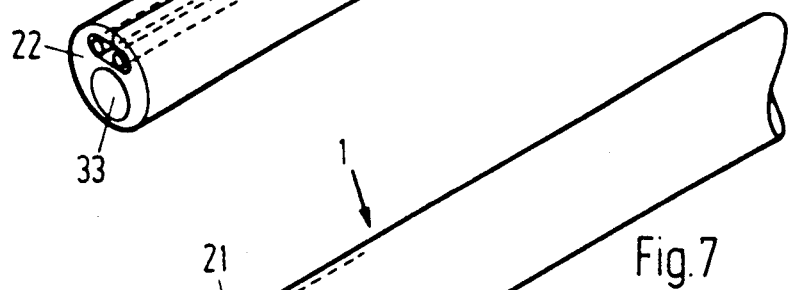
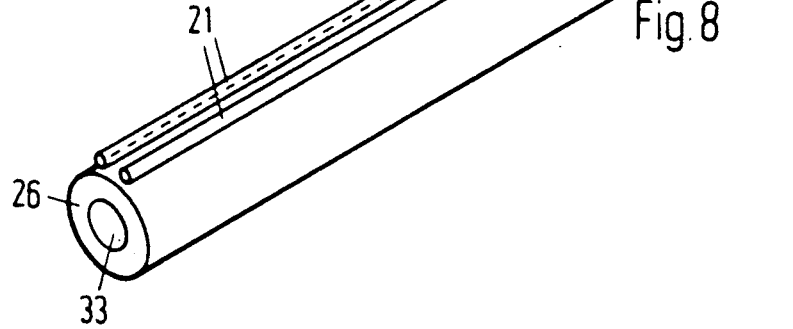

METHOD AND APPARATUS FOR FITTING OF A HEARING AID AND ASSOCIATED PROBE WITH DISTANCE MEASURING MEANS

The invention relates to a method for the fitting of a hearing aid to an ear through the use of distance measuring means employing light.

It is known to vary the frequency curve of an electrical hearing aid depending on the hearing ability. In fitting a person with a hearing aid, an attempt is also made to take the resonance of the auditory canal into consideration, as this is very individual. The function of a hearing aid depends on the resonance of the individual auditory canal.

The attempts hitherto made to measure the resonance of the auditory canal and to set the hearing aid accordingly have not been satisfactory, the reason being that the measurements are strongly dependent on the positioning of the measuring probe in the auditory canal.

The probe must be placed at a predetermined, short distance from the ear drum, in that one hereby measures the sound pressure conditions in the auditory canal, and substantially in the manner as they are experienced by the person. If the distance is changed, the results obtained from the measurement are extremely divergent, and therefore it is very important that the distance is maintained precisely during the two courses of measurement, in that one first measures the sound pressure conditions with the open ear, and thereafter the sound pressure conditions with the hearing aid inserted in the ear and switched on. The two measurements are normally made in that the frequency of the applied acoustic signal is swept over the whole of the audible range, i.e. from approx. 100 Hz to approx. 10 kHz. By subtracting the result of the last measurement from the result of the first measurement, a curve is obtained showing the insertion gain for the relevant hearing aid placed in the relevant ear. On this basis, one can now adjust the frequency characteristic of the hearing aid, among other things while paying regard to the user's hearing impairment. Therefore, this adjustment takes place while taking into consideration the actual sound pressure conditions in the auditory canal.

The object of the invention is to present a method by which the sound pressure conditions in the auditory canal of a hearing aid user can be measured with very great precision and with a very high degree of uniformity.

This is achieved by the method and apparatus described herein. The precise position of the probe in relation to the ear drum is constantly known, and it can thus be ensured that all measurements are undertaken with the probe at a certain distance from the ear drum. The measurements obtained hereby are reproducible, which means that later measurements can be compared with measurements made earlier. Moreover, the risk of touching the ear drum with the probe during the measuring procedure is considerably reduced, which is very important since it is very unpleasant if the probe touches the ear drum. The distance measurements according to the invention can be effected with audio signals or light signals, e.g. by the application of ultrasonic waves or red or yellow light. The methods of measurement achieved hereby are in no way unpleasant for the person on which the measurements are being made. The distance measurements can be carried out by measuring the signal strength of the reflected audio or light signal or, if pulse-modulated signals are used, the distance is measured by measuring the difference in time between the emission and the receipt of a pulse. Moreover, the method of measurement ensures that only the reflections from the ear drum are measured, and not reflections from the wall of the auditory canal, e.g. if there is a curvature in the wall of the canal.

The invention also relates to an apparatus for use in the fitting of hearing aids, including a signal source, reference microphone, measuring probe and processor.

By configuring the apparatus as described above the sound pressure conditions can be measured as a function of the frequency in the auditory canal of a hearing aid user, and the insertion gain, in situ gain, functional gain etc. can be calculated with a certainty and accuracy which can be used for a considerably improved setting of the frequency response in the hearing aid than has hitherto been possible.

By configuring the apparatus to produce a measuring wave of either sound, electromagnetic waves or light, one can obtain precise, reproducible measurements, without the person on whom the measurements are being made feeling any unpleasantness while the measurements are taking place, which contributes greatly to a better fitting of the hearing aid, in that in certain cases it is necessary to repeat the measurements several times before a completely optimal setting of the hearing aid's frequency response is achieved.

By configuring the probe to use focused light in the measuring means, precise measurements are ensured, in that the light conductors throw the light forwards in a certain direction in relation to the probe, hereby avoiding incorrect measurements.

The apparatus according to the invention is preferably configured to include calibration means to determine measuring accuracy. This hereby enables the precision of the distance measurement elements to be adjusted before the sound-pressure measurements are carried out. This makes it possible to use probes of cheaper materials for once-only use, particularly where light conductors of a poorer quality are used. Throw-away probes are to be preferred for reasons of hygiene.

Figure 9:
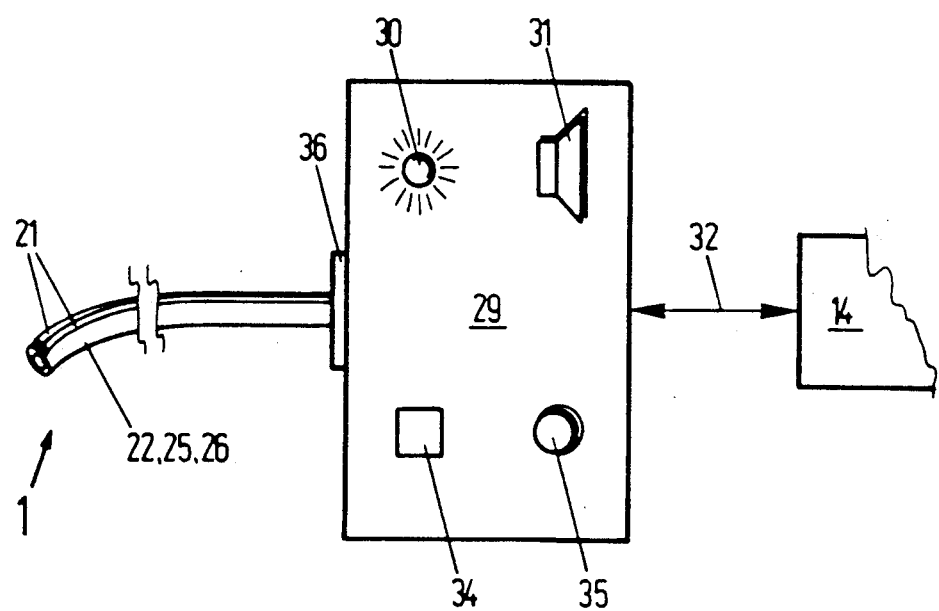
Figure 10:
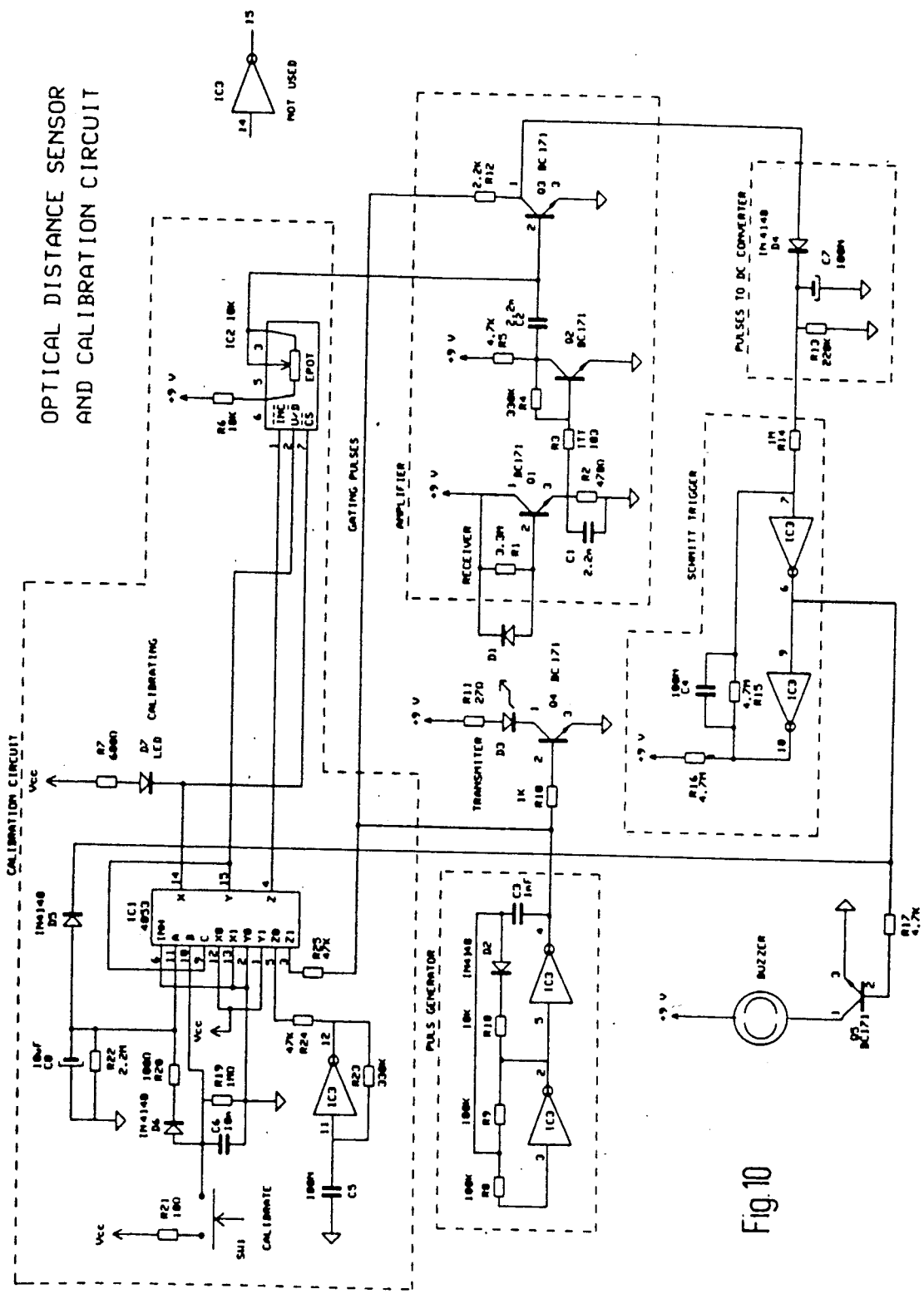

The invention also relates to a probe for an apparatus used for the fitting of hearing aids, said probe being configured to include a tube and measuring means such that the tube and measuring means are connected on one end to a measuring circuit. The whole of the probe can be designed for once-only use, in that both the probe for the measurement of the sound pressure and the means for measuring the distance are replaced as a unit after use. Such probes are particularly advantageous for measuring apparatus with calibration element, The invention will now be described in more detail with reference to the drawing, which shows both the known method for the measurement of insertion gain as well as the method, the apparatus and the probe according to the invention, in that FIG. 1 shows how attempts have hitherto been made to measure the sound-pressure levels in the auditory canal in the ear of a person, FIG. 2 shows curves covering the sound pressure measured as a function of the frequency and depending on the position of the probe in the auditory canal, FIG. 3 shows a measuring apparatus which is used to carry out the measurements shown in FIGS. 1 and 2, FIG. 4 shows the calculation of insertion gain on the basis of a measurement of the sound-pressure levels in the auditory canal, FIG. 5-8 show various embodiments of the measuring probe for use with the method and the apparatus according to the invention, FIG. 9 shows a measuring probe according to the invention coupled to an electronic measuring circuit, FIG. 10 shows an example of an electronic distance measuring circuit.

Figure 2:
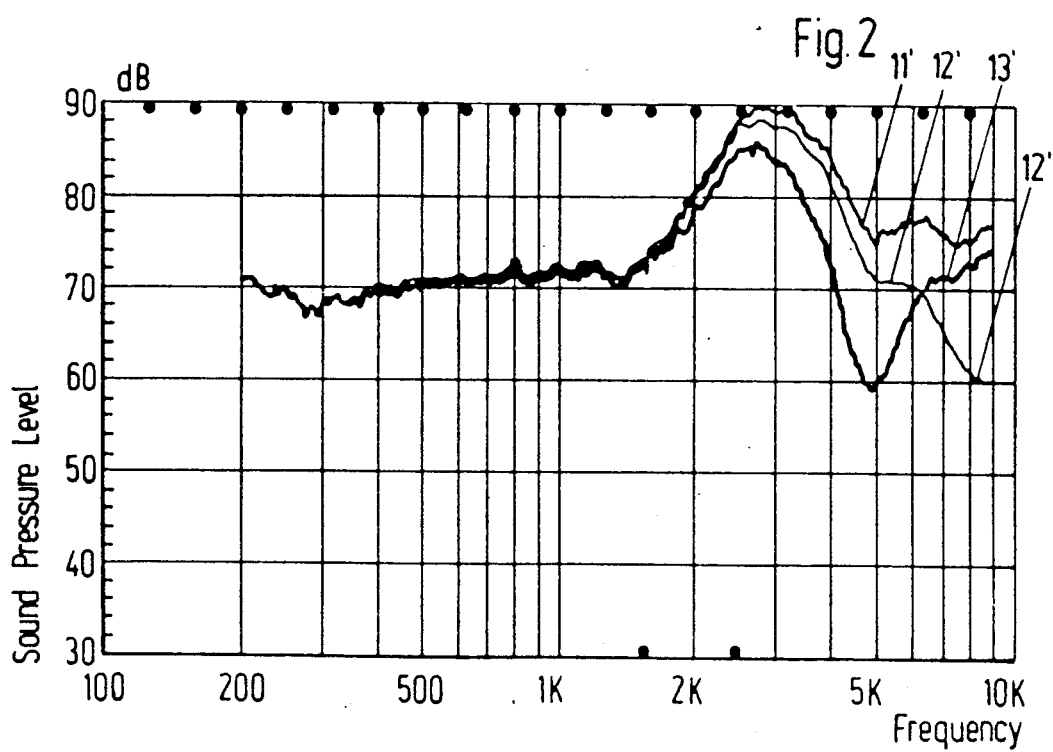
Figure 3:
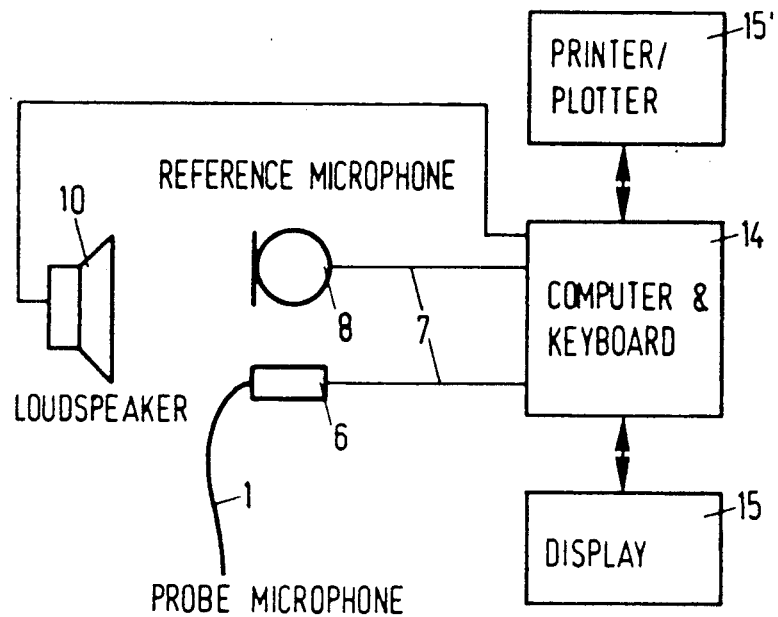
Figure 4:
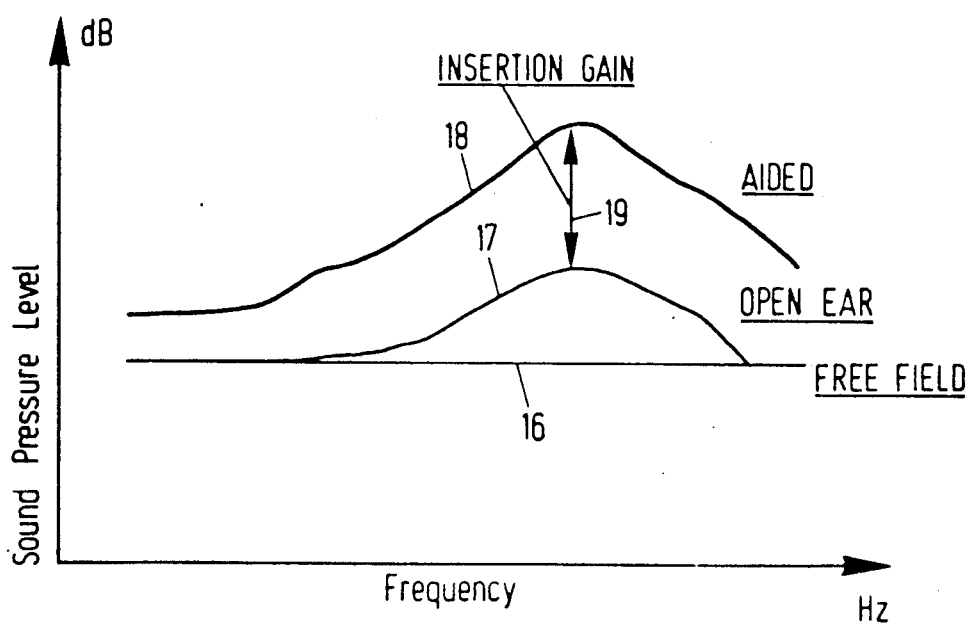

FIGS. 1-3 illustrate a known method used in the fitting of a hearing aid, whereby a probe in the form of a tube is inserted into the auditory canal. In FIG. 1, the reference FIG. 3 indicates the ear drum and 9 the inner ear. On the inserted tube 1 there is a mark 2 which must lie just opposite the tragus 5. The person is then placed at a predetermined distance from a sound source 10, the frequency of which is then swept while at the same time the signal received by the probe 1 is registered in a data processing unit 14 with display 15 and printer or plotter 15', see FIG. 3. The tube 1 is coupled to a microphone unit 6, possibly with a built-in amplifier. There is also used a reference microphone 8 for measuring the sound level immediately at the inlet to the ear. The sound pressure measured from the reference microphone 8 and the probe microphone 6 is fed to the data processing unit 14 by means of the leads 7. The sound pressure measured by the reference microphone 8 is used for the automatic setting of the data processing unit 14, so that the generator built herein is always adjusted in such a manner that at any given frequency, the sound source 10 will provide the same sound pressure at the reference microphone 8. The measurement set-up shown in FIG. 3 can, for example, comprise the Danavox Measurement System Type CAS or the Madsen Electronics Type IGO 1000. The probe 1 is a flexible tube with a diameter in the order of 1-2 mm and a length of 3-10 cm.

In FIG. 2 will be seen the sound-pressure signals measured by the microphone 6, in that the sound pressure at the reference microphone 8 is always constant. Since the auditory canal constitutes an acoustic resonator, the signal received by the probe 1 depends strongly on the positioning of the probe in the auditory canal. At three different positions of the probe's free end, namely the positions marked 11, 12, 13 in FIG. 1, the sound pressure curves 11', 12' and 13' shown in FIG. 2 were measured. In order to obtain accurate measurements, it is of interest to be able to place the probe all the way in to the ear drum 3, though without touching the ear drum. By placing the probe close to the ear drum, the best expression is obtained of what is heard by the person.

Alternatively, the probe could be placed at a predetermined distance from the ear drum 3, and thereafter a mathematical correction could be made of the measurement results. Such a correction is difficult to carry out, in that regard must be paid to the length and shape of the auditory canal. The best thing would be if the probe 1 could be placed at a distance of approx. 1 mm from the ear drum 3. However, it is difficult to do this while making sure that the probe does not touch the ear drum, the reason being that the length and shape of the auditory canal differ greatly from person to person.

One of the measurements it is desirable to be able to make is the measurement of the insertion gain, which is shown and explained in connection with FIG. 4.

The curve 16 shown in FIG. 4 indicates the sound pressure measured with the reference microphone 8. The sound pressure applied to the person's ear is thus held constant for all frequencies.

The curve 17 shows measurements with the free end of the probe 1 placed at a fixed distance from the ear drum 3. Nothing other than the probe 1 is inserted in the auditory canal, and thus the measurement is characterized as an "open ear" measurement.

The curve 18 shows the measurement of the sound pressure with the free end of the probe 1 at the same fixed distance from the ear drum 3, but with a hearing aid placed in the ear and switched on. This measurement curve is thus characterized in the drawing as "aided".

The difference 19 between the curves 18 and 17 is what is termed the insertion gain. On the basis of this frequency-dependent insertion gain, an expert can evaluate whether the hearing aid is set correctly, or whether the frequency response must be adjusted. After a possible adjustment of the hearing aid, the whole of the measuring procedure can be repeated until the insertion gain is suitable in relation to the hearing impairment that the person has in the relevant ear.

The difficult measurement is that of the curve 18, in that the insertion of the hearing aid, e.g. an all-in-the-ear aid, or the earplug from a behind-the-ear aid, can very easily displace the probe 1 so that the position of the free end of the probe in relation to the ear drum is easily changed.

According to the invention, it is disclosed how a probe 1 will be able to be placed at a predetermined and substantially very short distance from the ear drum 3 without risk of touching the ear drum. The free end of the tube introduced into the auditory canal is located with the help of one or more light conductors 21, which are placed in or at the tube. The one light conductor is used for the emission of, for example, red or yellow light, while the other light conductor is used to receive it. One now utilizes the fact that both the transmitting light conductor as well as the receiving light conductor have an emission characteristic substantially as shown in FIG. 5. At any distance from the the ear drum 3, the signal received will be of a certain magnitude. Moreover, it is seen that there will be a uniform relationship between distance and signal strength, and that therefore it is possible to carry out a calibration which enables the distance of the probe to the ear drum 3 to be indicated on the basis of the strength of the signal.

One can also use the difference in time between the transmission and receipt of a light pulse. This time diference is in the order of 10-30 pSec., and is a measurement of the distance to the ear drum. The electronic signal processing circuit associated herewith comprises quick timing circuits built up of GaAs components.

In another emodiment, the distance to the ear drum is measured by means of an ultrasonic signal emitted from a transducer mounted on the inserted tube, in that the difference in time from transmission to receipt of an ultrasonic pulse is an expression of the distance to the ear drum.

FIG. 5 shows in principle a probe 1 comprising a tube with through-going clearance 33 and two moulded-in light conductors 21. The light conductors can be disposed in such a manner that the light 20 from the transmitting light conductor is emitted in extension of the probe, and such that it does not fall to any considerable degree outside the extension of the probe's outer periphery. The reference number 27 indicates how that light conductor which captures the light reflected from the ear drum is also directed forwards, and is primarily sensitive to reflected light within the extension of the probe's outer periphery. This can be brought about when the light conductors at the free end of the probe are angled in relation to the longitudinal axis of the probe, or by shaping of the terminating edge on the light conductors.

FIG. 6 shows an embodiment of the probe 1 in which the light conductors 21 are disposed in a longitudinal cavity 23, possibly having a longitudinal slot 24 for use in the insertion of the light conductors. The actual tube 22 is thus given an irregular wall thickness, but this is of no significance to the results of the measurements, merely providing that the clearance 33 can be held open for the whole length of the tube during the measurements.

FIG. 7 shows another embodiment in which the light conductors 21 are moulded-in diagonally to the clearance 33 in the tube 25.

FIG. 8 shows a further embodiment in which the light conductors 21 are disposed externally on the tube 26. In practice, it is sufficient for the light conductors to be secured to the tube 26 in an area at its free end, so that the direction of the light conductors in this area is the same as that of the tube. Moreover, as shown in FIG. 8, the light conductors 21 can be drawn back a short distance in relation to the free end of the tube 26, thus more easily avoiding that the light conductors get smeared with earwax. This also applies to the embodiments shown in FIGS. 5-7.

FIG. 9 shows a probe 1 as a unit with a plug element or a holder 36 which can be mounted with an electronic measuring circuit 29 which replaces the microphone unit 6 in FIG. 3.

The whole probe 1 comprises a tube 22, 25, 26, the light conductors 21 and the plug element 36, and can ne configured as a replaceable unit for once-only use.

The electronic measuring circuit 29 is provided with measuring elements for the measurement of the distance from the free end of the probe to the ear drum. When light conductors 21 and light is used for the distance measurement, this part of the circuit can be comprised of the electronic circuit shown in FIG. 10.

FIG. 10 shows an optical distance measuring circuit comprising an optical transmitter with pulse generator, and an optical receiver with amplifier and associated calibration circuit and pulse and trigger circuits. FIG. 10 is merely an example of how such a measuring circuit can be configured.

In the electronic measuring circuit 29, the reference number 30 indicates a signal lamp, e.g. a light diode, and 31 an acoustic signal element, e.g. a miniature loudspeaker, in that the whole of the measuring circuit can be set in such a manner that the signal elements inform when a predetermined distance, e.g. of 1 mm, has been reached.

The measuring circuit 29 can include a calibration element 34, 35 for the calibration of the probe 1. When the probe with the plug 36 is mounted on the measuring circuit, the free end of the probe is inserted in the opening 34 and the pushbutton 35 is activated. In the opening 34 can be placed a holder with a well-defined distance, e.g. 1.0 mm. When the pushbutton 35 is activated, the whole of the electronic measuring circuit is adjusted, so that possible tolerances and inaccuracies in the probe 1, or inaccuracies in connection with the coupling of the plug 36, are introduced into the measuring circuit as correction values, so that the probe will hereafter measure the distance in a completely precise manner. When the automatic adjustment has been concluded and is in order, the measuring circuit 29 will, via the signal elements 30, 31, inform that this is the case, after which the measuring probe can be used as described above.

We claim:

1. Method for the fitting of a hearing aid to an ear, whereby:
    a) an acoustic signal in the audible range is applied to the ear,
    b) the sound pressure at the inlet to the outer ear is measured, the result of said measurement being used for adjusting the amplitude of the applied acoustic signal,
    c) the sound pressure is measured at a position in the vicinity of the ear drum using a measuring probe comprising a tube having an end inserted in the auditory canal, and with open ear,
    d) the sound pressure is measured at said position in the vicinity of the ear drum and with said measuring probe, but with a hearing aid device place correctly in the ear,
    e) the sound pressures measured under c) and d) above are fed to an electronic circuit for the formation of the difference between the sound pressure measured with the hearing aid device and the sound pressure measured without the hearing aid, said difference being used for the adjustment of the hearing aid device, characterized in that the measuring probe tube end comprises means for the measurement of the distance between the probe tube end and the ear drum, said measurement being carried out by the emission of light and the receiving of reflected light, in that the distance measurement is effected by scanning he time difference between the emission and reception of the light with a measuring circuit for the distance measurement.

2. Method according to claim 1, wherein said hear aid device comprises a hearing aid sounding body.

3. Method according to claim 1, wherein said measuring circuit comprises signal elements.

4. Method according to claim 1, wherein said measuring circuit comprises display elements.

5. Apparatus for use in the fitting of a hearing aid and comprising:
    a) a signal source (10) arranged to emit an acoustic signal in the audible frequency range,
    b) a reference microphone (8) for the measuring of the sound pressure created by the signal source at the inlet to the user's ear, and with means (14) for the regulation of the strength of the signal source,
    c) a measuring probe (1) comprising a tube having an end inserted in the auditory canal, with microphone for the measurement of the sound pressure in the vicinity of the ear drum (3),
    d) a data processing unit (14) for the calculation of the measured sound pressure levels, characterized in that the measuring probe (1) tube end comprises means (21, 29) for the measurement of the distance between the probe tube end and the ear drum comprising a light source with means for conducting light to the measuring probe tube end, means for receiving light reflected off of the ear drum and conducting the reflected light to a measuring circuit for calculating the distance between the tube end and the ear drum by measuring the time difference between emission and reception of light from the light source.

6. Apparatus according to claim 5, characterized in that the means for conducting light conducts light forwards (20) in the probe's axial direction, and not substantially outside the extension of the outer periphery of the probe, and that the means for receiving and conducting reflected light is directed substantially in the same direction.

7. Apparatus according to claim 5, characterized in that the measuring circuit (29) further comprises means (30, 31) for producing signals when the probe (1) tube end is at a certain distance from the ear drum.

8. Apparatus according to claim 5, characterized in that the measuring circuit (29) further comprises a calibration element (34, 35) for the adjustment of the measuring accuracy of the means for the measurement of the distance between the probe tube end and the ear drum.

9. Apparatus according to claim 5, wherein said light source produces light which is pulse modulated.

10. Apparatus according to claim 5, wherein said means for conducting light is secured to the measuring probe tube end.

11. Apparatus according to claim 5, wherein said means for conducting light is disposed inside said measuring probe tube.

12. Apparatus according to claim 5, wherein said measuring probe further comprises an amplifier for measuring the sound pressure in the vicinity of the ear drum.

13. Apparatus according to claim 5, wherein said data processing unit further comprises a display means for displaying the measured sound pressure levels.

14. Apparatus according to claim 5, wherein said data processing unit further comprises a printer means for printing the measured sound pressure levels.

15. Probe apparatus for use in the fitting of a hearing aid during the measurement of the sound pressure levels in the auditory canal of a person, characterized in that the apparatus comprises at least one tube (22, 25, 26) having a free end and means (21) for conducting light distance measurement signals from a measuring circuit (29) to the tube's free end and reflected light signals in the opposite direction, in that both the tube and the means, at an end which is opposite the tube's free end, are secured in a holder (36) which is arranged to allow the tube and the means to be coupled to the measuring circuit (29) as a replaceable unit.

* * * * *